US006284956B1

(12) United States Patent
Rodriguez et al.

(10) Patent No.: US 6,284,956 B1
(45) Date of Patent: Sep. 4, 2001

(54) PLANT SELECTABLE MARKER AND PLANT TRANSFORMATION METHOD

(75) Inventors: Raymond L Rodriguez; Ning Huang, both of Davis, CA (US)

(73) Assignee: Applied Phytologics, Inc., Sacramento, CA (US)

( * ) Notice: Subject to any disclaimer, the term of this patent is extended or adjusted under 35 U.S.C. 154(b) by 0 days.

(21) Appl. No.: 09/344,438

(22) Filed: Jun. 25, 1999

Related U.S. Application Data

(60) Provisional application No. 60/090,896, filed on Jun. 25, 1998.

(51) Int. Cl.[7] ............................ C12N 15/29; C12N 15/82; C12N 15/54; C12N 15/56; A01H 5/00
(52) U.S. Cl. .................. 800/320.2; 800/278; 800/287; 800/293; 435/69.1; 435/194; 435/204; 435/209; 435/320.1; 435/418; 435/419; 435/468; 435/470
(58) Field of Search ........................ 800/278, 287, 800/293, 320, 320.2; 435/69.1, 194, 204, 209, 320.1, 418, 419, 468, 470

(56) References Cited

U.S. PATENT DOCUMENTS 5,420,034 * 5/1995 Kridl et al. ..................... 435/240.4

FOREIGN PATENT DOCUMENTS

WO 93/05164 3/1993 (WO) .

OTHER PUBLICATIONS

Hadi et al. Plant Cell Reports 15: 500–505, 1996.*
Li et al. Plant Cell Reports 12: 250–255, 1993.*
Simmons et al. Plant Molecular Biology 18:33–45, 1992.*
Kim et al. Plant Molecular Biology 24:105–117, 1994.*
Mol. Biol. of the Cell, Garland Publishing, Inc., New York, NY pp. 551–612, 1989.*
Chan et al. Plant Mol. Biol. 22: 491–506, 1993.*
Chen, L., et al., "Expression and inheritance of multiple transgenes in rice plants" *Nature Biotechnology* 16:1060–1064 (1988).
Michelmore, R., "Big news for plant transformation" *Nature Biotechnology* 14:1653–1654 (1996).
Shimamoto, K., et al., "Fertile transgenic rice plants regenerated from transformed protoplasts" *Nature* 338:274–276 (1989).
Shizuya, H., et al., "Cloning and stable maintenance of 300–kilobase–pair fragments of human DNA in *Escherichia coli* using an F–factor–based vector" *Proc. Natl. Acad. Sci. USA* 89:8794–8797 (1992).
Yang, D., et al., "Construction of a bacterial artificial chromosome (BAC) library and identification of overlapping BAC clones with chromosome 4–specific RFLP markers in rice" *Theor Appl Genet* 95:1147–1154 (1997).

* cited by examiner

*Primary Examiner*—David T. Fox
(74) *Attorney, Agent, or Firm*—Linda R. Judge; Perkins Coie LLP

(57) ABSTRACT

A plant transformation expression cassette for transforming host plant cells with a selectable marker gene is disclosed. The cassette includes, operatively linked in sequence in a 5' to 3' direction, (i) a DNA promoter sequence from the rice beta-glucanase 9 (gns9) gene; (ii) a selectable marker gene, and (iii) a 3' untranslated terminator region. Also disclosed are a expression cassette pair containing the transformation vector, a method of obtaining transformed monocots whose seeds produce a selected heterologous protein during sed germination, and a plant whose cells are transformed with the chimeric selectable marker gene.

10 Claims, 6 Drawing Sheets

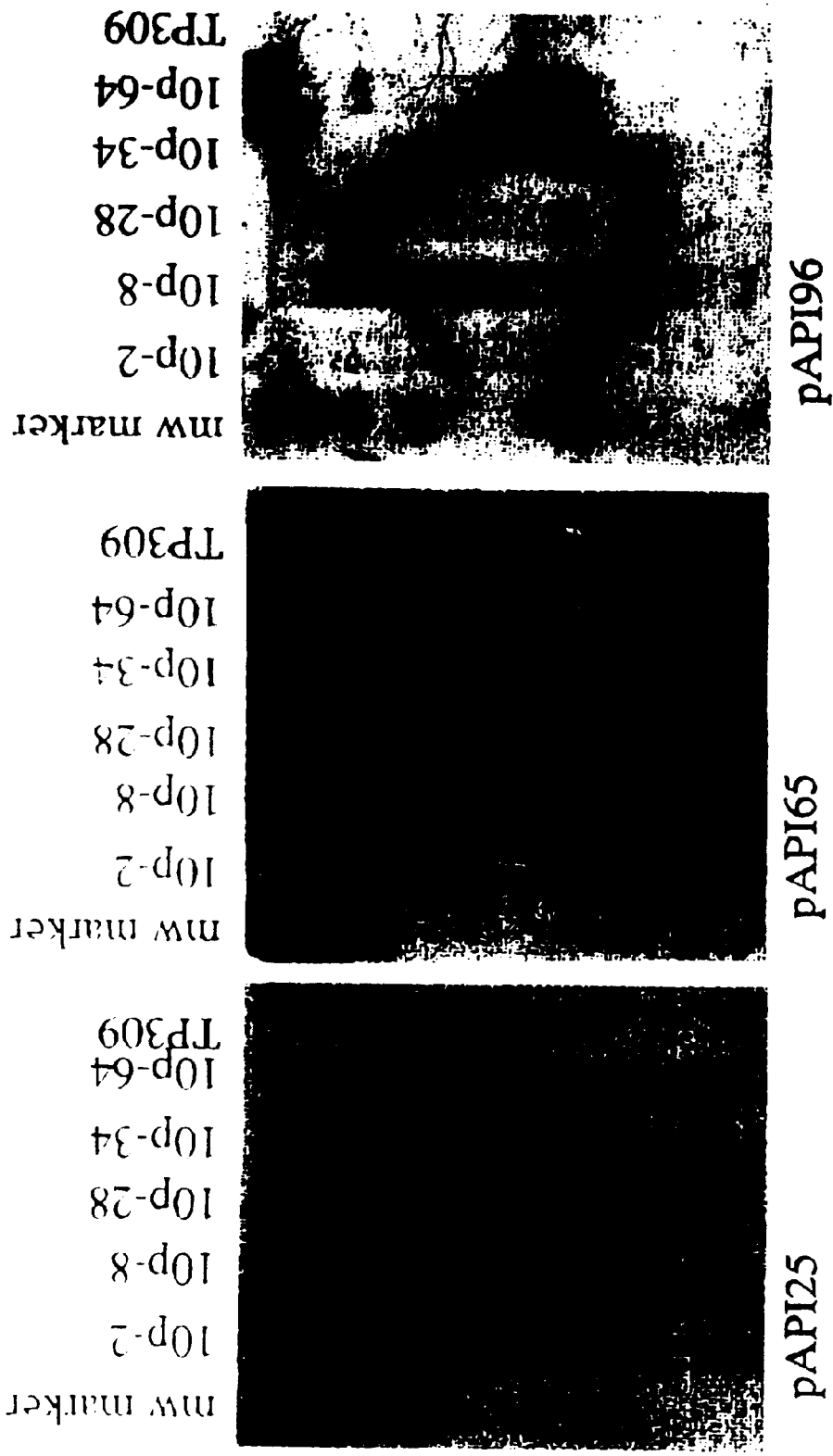

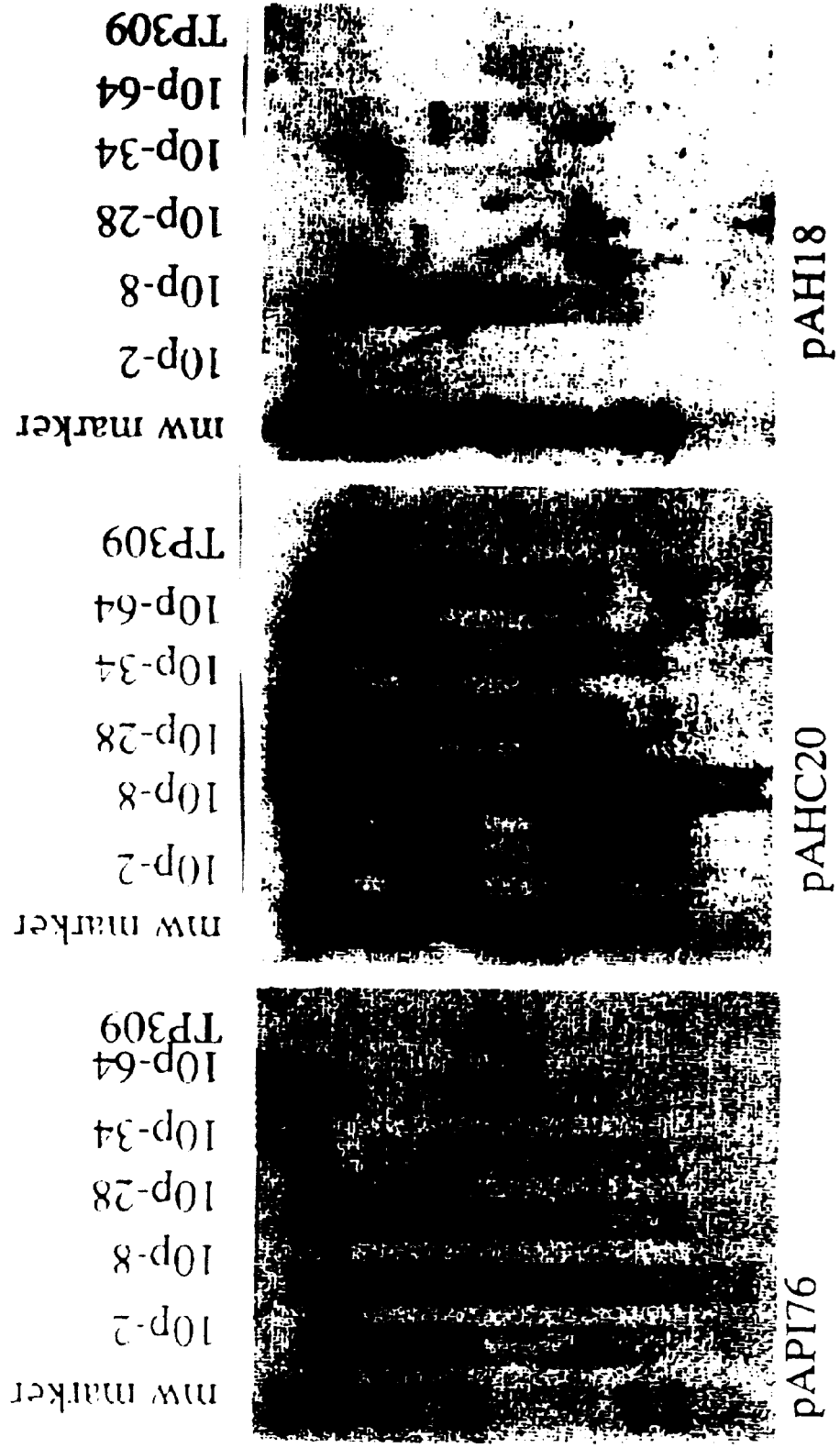

SEQUENCE LISTING

<160> NUMBER OF SEQ ID NOS: 12

<210> SEQ ID NO 1
<211> LENGTH: 955
<212> TYPE: DNA
<213> ORGANISM: Artificial Sequence
<220> FEATURE:
<223> OTHER INFORMATION: Gns9 promoter

<400> SEQUENCE: 1

```
ggatccaggg gacttaactt tagtccatat atttagacac taatttagag tattaaatat      60
aaattactta caaaactaat tcaataaatg aaagctaatt tgcgagacaa atttttatg      120 tttaattaat ccataattag agaatgttta ctgtagcatc acatagacta atcatggatt     180
aattaggctc aatagattcg tctcgtgaat tagtccaaga ttatggatgg attttattaa     240
tagtctacgt ttaatattta taattagtgt tcaaacatcc gatgtgatag ggacttaaaa     300
agtttagtcc catctaaaca gggccacagt ctatgtggag catgttcacc gaacaccgat     360
aaatattgca aagcccagaa tgattttggt cccacatgcc agaaactacc acacccacat     420
ttcggttcat tttcagctca ggaaaatcgt ccaacaattt cagctcagga aattaaatcg      480
tccgagaaag gaacaagttt ggagccgttg ggatgagagc aattaggtca cgcttaacta     540
caagtacagt ctcattcatc gacattgatt agccagcaac taaccactta accccgagcc      600
agcccaagcg ctccgtacgt tcgttgggcc cccgccgcgc aggcggagac aacggtcatc      660
cggcgcgccg gtcgctctcc ctcgctcgca cggccgcacc acccacttcg ccacgaaccc     720
gacgcgagcg cgacgtgcat ctcccaacat ccccgccatt tcctccccac ccaaaaccaa      780
cccgcccgcg tgcggctggc ccactttaca gcgcctcacc tcccccaacc ataaatcccc      840
gcccttttcc cccctctcc accactcacc acgctctcca ctacacgact cgtcgccgtc      900
ttgctctgct gcctctcgcg cccgcgcagc agtgagcagc agcaagagca gcaaa           955
```

<210> SEQ ID NO 2
<211> LENGTH: 2300
<212> TYPE: DNA
<213> ORGANISM: Artificial Sequence
<220> FEATURE:
<223> OTHER INFORMATION: Gns9-HPH-RAmy1A chimeric selectable marker gene

<400> SEQUENCE: 2

| | | | | | |
|---|---|---|---|---|---|
| aactttagtc | catatattta | gacactaatt | tagagtatta | aatataaatt acttacaaaa | 60 |
| ctaattcaat | aaatgaaagc | taatttgcga | gacaaatttt | ttatgtttaa ttaatccata | 120 |
| attagagaat | gtttactgta | gcatcacata | gactaatcat | ggattaatta ggctcaatag | 180 |
| attcgtctcg | tgaattagtc | caagattatg | gatggatttt | attaatagtc tacgtttaat | 240 |
| atttataatt | agtgttcaaa | catccgatgt | gatagggact | taaaaagttt agtcccatct | 300 |
| aaacagggcc | acagtctatg | tggagcatgt | tcaccgaaca | ccgataaata ttgcaaagcc | 360 |
| cagaatgatt | ttggtcccac | atgccagaaa | ctaccacacc | cacatttcgg ttcattttca | 420 |
| gctcaggaaa | atcgtccaac | aatttcagct | caggaaatta | atcgtccga gaaggaaca | 480 |
| agtttggagc | cgttgggatg | agagcaatta | ggtcacgctt | aactacaagt acagtctcat | 540 |
| tcatcgacat | tgattagcca | gcaactaacc | acttaacccc | gagccagccc aagcgctccg | 600 |
| tacgttcgtt | gggcccccgc | cgcgcaggcg | gagacaacgg | tcatccggcg cgccggtcgc | 660 |
| tctccctcgc | tcgcacggcc | gcaccaccca | cttcgccacg | aacccgacgc gagcgcgacg | 720 |
| tgcatctccc | aacatccccg | ccatttcctc | cccacccaaa | accaaccgc ccgcgtgcgg | 780 |
| ctggcccact | ttacagcgcc | tcacctcccc | caaccataaa | tccccgccct tttccccccc | 840 |
| tctccaccac | tcaccacgct | ctccactaca | cgactcgtcg | ccgtcttgct ctgctgcctc | 900 |
| tcgcgcccgc | gcagcagtga | gcagcagcaa | gagcagtcta | gaactagtgg atcccggggg | 960 |
| gcaatgagat | atgaaaaagc | ctgaactcac | cgcgacgtct | gtcgagaagt ttctgatcga | 1020 |
| aaagttcgac | agcgtctccg | acctgatgca | gctctcggag | ggcgaagaat ctcgtgcttt | 1080 |
| cagcttcgat | gtaggagggc | gtggatatgt | cctgcgggta | aatagctgcg ccgatggttt | 1140 |
| ctacaaagat | cgttatgttt | atcggcactt | tgcatcggcc | gcgctcccga ttccggaagt | 1200 |
| gcttgacatt | ggggaattca | gcgagagcct | gacctattgc | atctcccgcc gtgcacaggg | 1260 |
| tgtcacgttg | caagacctgc | ctgaaaccga | actgcccgct | gttctgcagc cggtcgcgga | 1320 |
| ggccatggat | gcgatcgctg | cggccgatct | tagccagacg | agcgggttcg cccattcgg | 1380 |
| accgcaagga | atcggtcaat | acactacatg | gcgtgatttc | atatgcgcga ttgctgatcc | 1440 |
| ccatgtgtat | cactggcaaa | ctgtgatgga | cgacaccgtc | agtgcgtccg tcgcgcaggc | 1500 |
| tctcgatgag | ctgatgcttt | gggccgagga | ctgccccgaa | gtccggcacc tcgtgcacgc | 1560 |
| ggatttcggc | tccaacaatg | tcctgacgga | caatggccgc | ataacagcgg tcattgactg | 1620 |
| gagcgaggcg | atgttcgggg | attcccaata | cgaggtcgcc | aacatcttct tctggaggcc | 1680 |
| gtggttggct | tgtatggagc | agcagacgcg | ctacttcgag | cggaggcatc cggagcttgc | 1740 |
| aggatcgccg | cggctccggg | cgtatatgct | ccgcattggt | cttgaccaac tctatcagag | 1800 |
| cttggttgac | ggcaatttcg | atgatgcagc | ttgggcgcag | ggtcgatgcg acgcaatcgt | 1860 |
| ccgatccgga | gccgggactg | tcgggcgtac | acaaatcgcc | cgcagaagcg cggccgtctg | 1920 |
| gaccgatggc | tgtgtagaag | tactcgccga | tagtggaaac | cgacgcccca gcactcgtcc | 1980 |
| gggatccccc | ctacgcaacc | cgggagaaaa | tctgagcgca | cgatgacgag actctcagtt | 2040 |
| tagcagattt | aacctgcgat | ttttaccctg | accggtatac | gtatatacgt gccggcaacg | 2100 |

-continued agctgtatcc gatccgaatt acggatgcaa ttgtccacga agtacttcct ccgtaaataa 2160
agtaggatca gggacataca tttgtatggt tttacgaata atgctatgca ataaaatttg 2220
cactgcttaa tgcttatgca tttttgcttg gttcgattgt actggtgaat tattgttact 2280
gttcttttta cttctcgaat 2300

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
aacaatactg gaattcgaga agtaaaaag                                  29

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
ctacgcaacc cgggagaaaa tc                                         22

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
gacttaactt tagtcatatt tag                                        23

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
ttcgctcttg ctgctgctca ct                                         22

<210> SEQ ID NO 7
<211> LENGTH: 49
<212> TYPE: DNA
<213> ORGANISM: Artificial Sequence
<220> FEATURE:
<223> OTHER INFORMATION: primer

<400> SEQUENCE: 7
gcagtctaga actagtagat ctcgggggc aacgaaatat gaaaaagcc              49

<210> SEQ ID NO 8
<211> LENGTH: 49
<212> TYPE: DNA
<213> ORGANISM: Artificial Sequence
<220> FEATURE:
<223> OTHER INFORMATION: primer

<400> SEQUENCE: 8 ggcttttttca tatttcgttg cccccccgaga tctactagtt ctagactgc           49

```
<210> SEQ ID NO 9
<211> LENGTH: 47
<212> TYPE: DNA
<213> ORGANISM: Artificial Sequence
<220> FEATURE:
<223> OTHER INFORMATION: primer

<400> SEQUENCE: 9
taatggatcc tcattcctat tcctttgccc tcggacgagt gctgggg                47

<210> SEQ ID NO 10
<211> LENGTH: 26
<212> TYPE: DNA
<213> ORGANISM: Artificial Sequence
<220> FEATURE:
<223> OTHER INFORMATION: primer

<400> SEQUENCE: 10
atcgccgcgg ctccgggcgt atatgc                                       26

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
attgcaagcg aaccggaatt gccag                                        25

<210> SEQ ID NO 12
<211> LENGTH: 23
<212> TYPE: DNA
<213> ORGANISM: Artificial Sequence
<220> FEATURE:
<223> OTHER INFORMATION: primer

<400> SEQUENCE: 12
aaactcttcc tttttcaatt cag                                          23
```

PLANT SELECTABLE MARKER AND PLANT TRANSFORMATION METHOD

This application claims priority, under 35 U.S.C. § 119(e), to U.S. provisional patent application Ser. No. 60/090,896, filed Jun. 25, 1998.

FIELD OF THE INVENTION

The present invention relates to an expression cassette containing a selectable marker gene, for cotransforming a monocot plant, to plant transformation methods using the selectable marker expression cassette, and to plants and plant cells transformed with the selectable marker expression cassette.

BACKGROUNG OF THE INVENTION

Transgenic plants carrying one or more expressible heterologous genes in a transgene expression cassette have a variety of potential advantages. The plants carrying such a transgene expression cassette may carry one or more genes which confer herbicide tolerance, pesticide tolerance insect resistance, tolerance to stress, enhanced flavor or stability of the fruit or seed, or the ability to synthesize useful, non-plant proteins, e.g., medically valuable proteins or the ability to generate altered concentrations of plant proteins, and related impacts on the plant, e.g., altered levels of plant proteins catalyzing production of plant metabolites including secondary plant metabolites.

Ideally, the expression of the heterologous protein from the transgene expression cassette is largely confined to a particular differentiated plant tissue, e.g., the fruit or seed, and/or induced under selected conditions, e.g., plant hormone induction. To this end, it is desirable to place the gene encoding the heterologous protein in a gene expression cassette under the control of a promoter that is induced or inducible in a selected plant tissue, such as roots or leaves or seeds, and/or during selected plant induction states, such as seed maturation or seed germination.

There are multiple technologies, methods and biological materials that are needed in order to successfully genetically engineer a plant cell so that it can express recombinant molecules from a transgene expression cassette, and to make the transgenic plant cell commercially potentially usable and acceptable, including the following.

First, it is important to the success of methods used to transform plant cells to be able to readily and quickly detect successful transformant events. In the usual case, this means being able to screen cells for successful transformation within a few days to a few weeks of the transformation procedure. For many plants, including monocots, positive screening for successful transformants is performed most rapidly by co-transforming one or more transgene expression cassettes with a selectable marker expression cassette and conveniently by screening callus cells taken through the transformation process for a selectable marker in culture or on media plates.

The selectable marker gene in the selectable marker expression cassette is operably linked to selectable marker regulatory elements including a promoter and terminator. The expression in the transgenic plant cell of the selectable marker gene generally encodes a protein which confers resistance to an antibiotic or herbicide. Common selectable marker genes include, for example, the nptll kanamycin resistance gene, for selection in kanamycin-containing media, or the phosphinothricin acetyltransferase gene, for selection in media containing phosphinothricin (PPT), or the hph hygromycin phosphotransferase gene, for selection in media containing hygromycin B.

These selectable marker genes in the selectable marker expression cassette are expressed by promoters which are active in the undifferentiated callus tissues into which the selectable marker and heterologous genes are inserted. Heretofore, promoters generally used to drive expression of the selectable markers genes have been constitutive gene promoters, such as the Cauliflower Mosaic virus (CaMV) 35s promoter, the ubiquitin ubil promoter, and the actin promoter, have been constitutive promoters which express in a wide range of tissues, including the tissues in which expression of the heterologous gene is desired.

Second, it is important to the success of methods used to transform plant cells to be able to perform the transformation process in an efficient matter, that is, the process of plant cell transformation, selection and regeneration ought to require limited post-transformation manipulation of the plant tissue such as callus subjected to transformation, so as to enable processing of relevant number of transformed plant tissues so as to take advantage of items such as position effects.

Third, it may be important to the successful use and commercial acceptance of transgenic plant organs or tissues such as transgenic plant seeds in a food or feed formulation incorporating as ingredients transgenic plant seeds or extracts thereof, that the selectable marker protein not be present, or present only in very low amounts. In other words, the presence of the selectable marker protein in a transgenic seed for use in food or feed is potentially a negative or block to the food or feed use of said transgenic seed.

Finally, in many cases, it is useful to be able to simultaneously transform plant cells with one or more transgene expression cassettes. Such a procedure would allow the introduction of multiple transgenic traits in a single plant cell, e.g., multiple proteins promoting human or animal health in a single transgenic plant cell or transgenic plant tissue or organ such as a plant seed. Such a procedure would also allow for the introduction of multiple genes in a single plant transgenic plant cell with the intended purpose of using said genes in combination as a way to metabolically engineer a plant cell pathway, e.g., a pathway coding for plant secondary metabolites such as the phenylpropanoid pathway. Transformation and selection methods employing such promoters have generally not been successful and efficient in transforming monocot plants with multiple, e.g., 5–10, heterologous genes found in multiple transgene expression cassettes.

Heretofore, there have been no convenient methods, technologies and biological materials enabling efficient transformation events and selection and regeneration with the resulting transgenic plant tissues not expressing the selectable marker protein from the selectable marker expression cassette.

For example, the use of the double cassette vector or multiple single cassette vectors in conjunction with Agrobacterium transformation requires that the resulting transformants go through a breeding program in order to determine if it is possible to segregate the selectable marker expression cassette from the transgene expression cassette so as to get a transgenic plant and resulting seed carrying the transgene expression cassette but not the selectable marker expression cassette. This breeding program takes substantial time to the development of a product from a transgenic plant.

A similar problem is encountered with the use of the ballistic transformation methodology in which there is co-transformation of a selectable marker expression cassette with a constitutive promoter directing expression of the selectable marker gene, along with the transgene expression cassette. Again, in order to generate a transgenic plant cell and resulting transgenic plant or plant seed without the selectable marker protein, the selectable marker expression cassette and the transgenic expression cassette need to be genetically segregated using a breeding program, a timely procedure that limits the commercial utility transgenic protein.

The current invention solves these current problems. First, this invention includes a method of selecting and regenerating transgenic plants that significantly reduces the time and labor processing transgenic plant material. Second, the present invention includes a regulated promoter for use in controlling expression of the selectable marker gene during selection, but not after regeneration so that the resulting transgenic seed does not contain the selectable marker protein.

SUMMARY OF THE INVENTION

In one aspect, the invention includes a set of expression cassettes, including vectors containing expression cassettes, for use in transforming monocot plants with one or more heterologous genes capable of producing heterologous proteins in the monocot plant seeds, under selected induction conditions. The set includes: (a) a selectable marker expression cassette having, operatively linked in sequence in a 5' to 3' direction, (i) a regulated transcriptional regulatory region, (ii) a selectable marker gene, and (iii) a 3' untranslated terminator region; and (b) at least one heterologous gene expression cassette having, operatively linked in sequence in a 5' to 3' direction, (i) a transcriptional regulatory region that is induced or inducible in plant seeds, (ii) a first DNA sequence encoding a heterologous protein, and (iii) a 3' untranslated terminator region.

The regulated transcriptional regulatory region in the selectable marker expression cassette is one which expresses in transformed callus cells at a significantly higher level than in the selected target tissue, e.g., seeds, and hybridizes under conditions of high stringency with the rice β-glucanase gene promoter Gns-9 identified by SEQ ID NO:1. The promoter may be contained in the sequence identified by SEQ ID NO:1.

The transcriptional regulatory region in the heterologous-gene expression cassette is preferably induced or inducible during seed maturation or seed germination.

For use in transforming monocot plants by a plurality of heterologous genes, the set of expression cassettes may include a plurality of heterologous-gene expression cassettes, each having, operatively linked in sequence in a 5' to 3' direction, (i) a transcriptional regulatory region that is induced or inducible in plant seeds, (ii) a DNA sequence encoding a heterologous protein, and (iii) a 3' untranslated terminator region.

Alternatively, the expression cassettes for the selectable marker gene and one or more heterologous proteins may be carried, e.g., in tandem, in a single plant-transformation vector.

In another aspect, the invention includes a method for transforming monocot plants with one or more heterologous genes capable of producing heterologous proteins in the monocot plant seeds, under selected induction conditions. The method includes transforming plant callus cells with the set of expression cassettes described above; culturing the callus cells in the presence of a selection agent effective to block growth of callus cells, in the absence of expression of the selectable marker gene; selecting those callus cells that express the selectable marker, as evidenced by their growth in the presence of the selection agent; and regenerating the selected callus cells into transgenic plants under non-selection conditions.

Using either the concatenated heterologous-gene expression cassette above, or a plurality of individual heterologous gene expression cassettes, the method is effective to transform monocot plants with a plurality of heterologous genes, e.g., four or more genes, and as many as ten or more genes.

Also disclosed are transgenic monocot plants produced by the method of the invention, by transformation of callus cells with the set of expression cassettes of the invention, and transgenic seeds produced by the plants.

In still another aspect, the invention includes a plant transformation expression cassette for transforming monocot plant cells with a selectable marker gene containing, operatively linked in sequence in a 5' to 3' direction, (i) a transcriptional regulatory region which hybridizes under high-stringency conditions with a rice 0-glucanase gene promoter identified by SEQ ID NO:1, and which expresses in callus cells at a significantly higher level than in a selected target tissue, (ii) a selectable marker gene, and (iii) a 3' untranslated terminator region.

In various embodiments, the selectable marker gene may include, but is not limited to, the nptII kanamycin resistance gene, for selection in kanamycin-containing media, or a gene encoding phosphinothricin acetyltransferase, for selection in media containing phosphinothricin, or a gene encoding hygromycin phosphotransferase (HPH), for selection in media containing hygromycin B. In a preferred embodiment, the selectable marker gene encodes HPH. In other embodiments, the 3' untranslated terminator region is the 3' untranslated region from the rice alpha-amylase 1A (RAmy1A) gene, and the marker gene expression cassette the sequence identified by SEQ ID NO:2.

The invention also includes a transgenic monocot plant seeds containing a heterologous selectable marker gene under the control of a regulatory region that is induced in callus plant tissue, allowing selection of transgenic monocot callus tissue in a suitable selection medium, but is substantially dormant in seed maturation or germination, preventing expression of the marker gene at gene-selection levels in seeds, and a heterologous protein that is under the control of a regulatory region that is induced during seed maturation or germination.

Also forming part of the invention is a transgenic monocot plant seed containing at least four different expression cassettes, each containing a regulatory region that is induced in maturing or germinating seeds, a gene encoding a protein heterologous to monocot plants, and (iii) a 3'untranslated terminator region, and characterized by detectable expression of the expression cassette genes during seed maturation of germination.

These and other objects and features of the invention will become more fully apparent when the following detailed description of the invention is read in conjunction with the accompanying drawings.

BRIEF DESCRIPTION OF THE DRAWINGS

FIGS. 2A–2I are Southern blots showing the stable integration of nine heterologous genes (A–I), including the selectable marker gene, in transgenic plants by simultaneous transformation with nine plasmids using the improved selection/regeneration method of the invention in conjunction with regulated promoter-selectable marker construct of the present invention;

DETAILED DESCRIPTION OF THE INVENTION

Figure 1A:
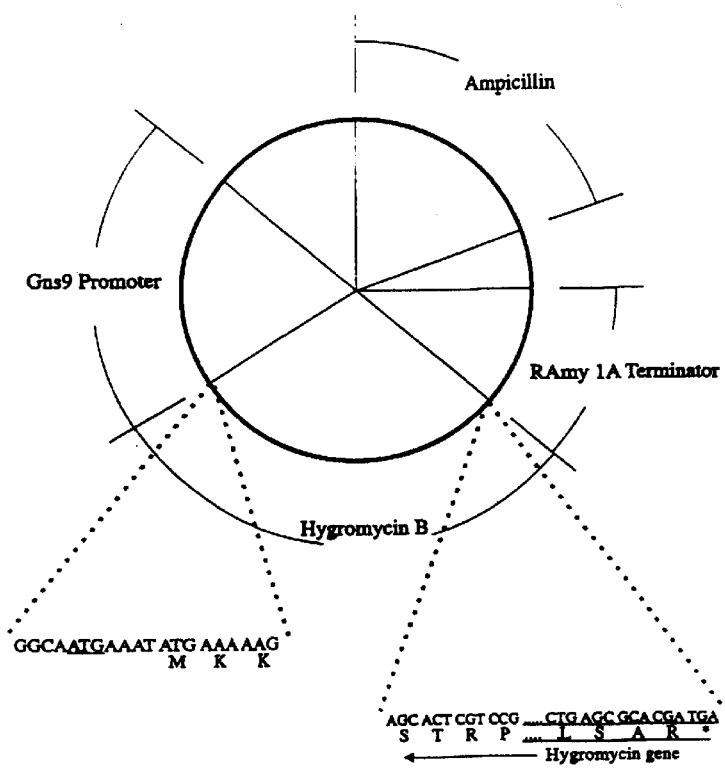
FIG. 1A shows the pAPI-76 selectable marker vector in accordance with one embodiment of the invention.

1. Definitions:

The terms below have the following meaning, unless indicated otherwise in the specification.

"Seed" means grain which includes the seed proper, the seed coat and/or the seed hull, or any portion thereof.

"Germination" refers to the breaking of dormancy in a seed and the resumption of metabolic activity in the seed, including the production of enzymes effective to break down starches in the seed endosperm.

"Seed maturation" or "grain development" refers to the period starting with fertilization in which metabolizable reserves, e.g., sugars, oligosaccharides, starch, phenolics, amino acids, and proteins, are deposited, with and without vacuole targeting, to various tissues in the seed (grain), e.g., endosperm, testa, aleurone layer, and scutellar epithelium, leading to grain enlargement, grain filling, and ending with grain desiccation.

A "regulatable" promoter is upregulated ("turned on" or "induced") or downregulated ("turned off") in response to a biochemical stimulus, such as the presence or absence of a small molecule, or in a particular tissue, e.g., callus tissue, root tissue, etc., or at a particular stage in plant development, e.g., undifferentiated callus cell vs differentiated plant tissue, or seed development stage, e.g., seed maturation or germintation.

A "constitutive" promoter is a promoter which is absent of any regulation, i.e., is unregulated.

"Inducible or induced" refers to a promoter that is upregulated by the presence or absence of a small molecule, or is upregulated in a particular tissue (e.g., callus tissue, or root tissue, etc.) or at a particular stage in plant development (e.g., during seed maturation).

"Inducible or induced during seed germination" refers to a promoter which is or can be upregulated significantly (greater than 25%) during seed germination.

"Inducible during seed maturation" refers to a promoter which is or can be upregulated significantly (greater than 25%) during seed maturation.

A promoter is "substantially dormant" if the gene the promoter regulates is expressed at substantially undetectable levels. As the term applies to a promoter controlling the expression of a selectable marker gene, the promoter is substantially dormant if the amount of selectable marker produced is below a threshold that can be discriminated by subjecting the plant cell or tissue to a suitable selection pressure, e.g., an antibiotic. For example, in the case of a seed, the selectable-marker gene promoter would be considered dormant during seed germination if it was impossible to discriminate between transformed (containing the selectable marker gene) and non-transformed germinating seeds (not containing the selectable-marker gene) on the basis of the presence of a suitable selection pressure, e.g., antibiotic.

"Small molecules", in the context of promoter induction, are typically small organic or bioorganic molecules less than about 1 kilodalton. Examples of such small molecules include sugars, sugar-derivatives (including phosphate derivatives), and plant hormones (such as, gibberellic or absissic acid), and environmental gases, such as $O_2$.

"Heterologous DNA" or "foreign DNA" refers to DNA, and typically to a DNA coding sequence ("heterologous coding sequence"), which has been introduced into plant cells from another source, that is, a non-plant source or from another species of plants, or a same-species coding sequence which is placed under the control of a plant promoter that normally controls another coding sequence. An insulin coding sequence placed under the control of a plant promoter is an example of a heterologous DNA, as is a rice β-glucanase coding sequence placed under the control of a barley α-amylase promoter.

A "transcription regulatory region" or "promoter" refers to nucleic acid sequences that influence and/or promote initiation of transcription. Promoters are typically considered to include regulatory regions, such as enhancer or inducer elements.

"Operably linked" refers to components of an expression cassette, function as a unit to express a heterologous protein. For example, a promoter operably linked to a heterologous DNA, which encodes a protein, promotes the production of functional MRNA corresponding to the heterologous DNA.

A "chimeric gene" or "expression cassette" in the context of the present invention, refers to a promoter sequence operably linked to DNA sequence that encodes a gene product, e.g., a selectable marker gene, or a desired heterologous gene, and preferably a transcription terminator sequence. The cassette may also contain a signal peptide coding region operably linked between the promoter and the gene product coding sequence in translation-frame with the gene product coding sequence, and may further contain transcription regulatory elements, such as the above-noted transcription termination signals, as well as translation regulatory signals, such as, termination codons.

A DNA sequence is "derived from" a gene, such as a rice β-glucanase gene, if it corresponds in sequence to a segment or region of that gene. Segments of genes which may be derived from a gene include the promoter region, the 5' untranslated region, and the 3' untranslated region of the gene.

A "product" encoded by a DNA molecule includes, for example, RNA molecules and polypeptides.

"Stably transformed" refers to a cereal cell or plant that has foreign nucleic acid stably integrated into its genome which is transmitted through multiple generations.

"Cell culture" refers to cells and cell clusters, typically callus cells, growing on or suspended in a suitable growth medium.

"Sequence identity" refers to the degree of identity between two sequences when those sequences are aligned using the "LALIGN" sequence alignment program (or analogous program) using default parameters. "LALIGN" is found in the FASTA version 1.7 suite of sequence comparison programs (Pearson, et al., 1988; Pearson, 1990; program available from William R. Pearson, Department of Biological Chemistry, Box 440, Jordan Hall, Charlottesville, Va.).

When a first polynucleotide fragment or polypeptide fragment is said to "correspond to" a second polynucleotide fragment or polypeptide fragment, respectively, it means that the fragments or regions are essentially co-extensive with one another when the sequences representing the fragments are aligned using a sequence alignment program, such as "LALIGN" or "MACVECTOR" (IBI, New Haven, Conn.). "Corresponding" polynucleotide or polypeptide fragments typically contain a similar, if not identical, number of residues. It will be understood, however, that corresponding fragments may contain insertions or deletions of residues with respect to one another, as well as some differences in their sequences.

"Hybridization" includes any process by which a strand of a nucleic acid joins with a complementary nucleic acid strand through base-pairing. Thus, strictly speaking, the term refers to the ability of the complement of the target sequence to bind to the test sequence, or vice-versa.

"Hybridization conditions" are based on the melting temperature (Tm) of the nucleic acid binding complex or probe and are typically classified by degree of "stringency" of the conditions under which hybridization is measured. For example, "maximum stringency" typically occurs at about Tm-5° C. (5° below the Tm of the probe); "high stringency" at about 5–10° below the Tm; "intermediate stringency" at about 10–20° below the Tm of the probe; and "low stringency" at about 20–25° below the Tm. Functionally, maximum stringency conditions may be used to identify sequences having strict identity or near-strict identity with the hybridization probe; while high stringency conditions are used to identify sequences having about 80% or more sequence identity with the probe.

An example of "high stringency" conditions includes hybridization at about 65° C. in about 5× SSPE and washing conditions of about 65° C. in about 0.1× SSPE (where 1× SSPE=0.15 sodium chloride, 0.010 M sodium phosphate, and 0.001 M disodium EDTA).

Two nucleotide sequences are considered to be "functionally homologous" if they hybridize with one another under moderately stringent conditions, i.e. 0.1% SSC at room temperature. Typically, two homologous nucleotide sequences are greater than or equal to about 60% identical when optimally aligned using the ALIGN program (Dayhoff, M. O., in ATLAS OF PROTEIN SEQUENCE AND STRUCTURE (1972) Vol. 5, National Biomedical Research Foundation, pp. 101–110, and Supplement 2 to this volume, pp. 1–10.).

II. Selectable-Marker Expression Cassette

The present invention includes a monocot plant transformation expression cassette containing a selectable marker gene which expresses a selectable marker at a substantially higher level in transformed callus tissue than in the target tissue. The cassette includes, in a 5' to 3' direction, (i) a transcriptional regulatory region, or promoter, which is a regulated promoter (ii) the selectable marker gene, and (iii) a 3' untranslated terminator region.

The cassette may be carried in a suitable vector, e.g., cloning vector or plant-transformation vector. This vector may additionally include, e.g., in tandem with the selectable marker cassette, one or more expression cassettes for expressing heterologous genes, for example, in maturing or germinating monocot plant seeds.

A. Transcription Regulatory Region

The transcriptional regulatory region, or promoter, is a regulated promoter which expresses in callus tissue at significantly higher levels than in selected target plant tissue. One preferred promoter is the rice β-glucanase-9 (Gns9) promoter. The Gns9 promoter, together with several other rice β-glucanase promoters, have been described in U.S. patent application Ser. No. 09/105,390, filed Jun. 25, 1998, which is incorporated by reference.

In a preferred embodiment, the transcriptional regulatory region has a nucleotide sequence which is effective to hybridize under high-stringency conditions to the Gns9 promoter having the sequence SEQ ID NO:1. In various other embodiments, the transcriptional regulatory region has a nucleotide sequence having at least 80% identity, preferably 90% identity, more preferably 95% identity, to the Gns9 promoter having the sequence SEQ ID NO:1.

In another embodiment, the transcriptional regulatory region has the Gns9 promoter sequence contained in SEQ ID NO:1. This promoter may include the entire sequence in SEQ ID NO:1, or operative portions thereof, as identified, for example, by conventional deletion analysis, in which a series of 5'-end deletions or 3'-end deletions, or internal deletions of SEQ ID NO:1 are made, and tested for the ability to promote the expression of a selectable marker in, for example, transformed callus tissue, as described below.

B. Selectable Marker Gene

A general review of suitable markers for the members of the grass family is found in Wilmink and Dons (1993) *Plant Mol. Biol. Reptr*, 11(2):165–185. Common selectable marker genes include, for example, the nptII kanamycin resistance gene, for selection in kanamycin-containing media, or the phosphinothricin acetyltransferase gene, for selection in media containing phosphinothricin (PPT), or the hph hygromycin phosphotransferase gene, for selection in media containing hygromycin B. In a preferred embodiment, a sequence encoding hygromycin phosphotransferase is used, and selection is performed in the presence of hygromycin B.

C. 3' Untranslated Terminator Region

The expression cassette typically has a transcriptional termination region at the opposite end from the transcription initiation regulatory region. The transcriptional termination region may normally be associated with the transcriptional initiation region or from a different gene. The transcriptional termination region may be selected, particularly for stability of the mRNA to enhance expression. Illustrative transcriptional termination regions include the NOS terminator from Agrobacterium Ti plasmid and the rice oa-amylase RAmy1A terminator.

The selectable-marker cassette may be constructed according to standard recombinant construction methods such as outlined in U.S. Pat. Nos. 5,889,189 and 5,888,789, which are incorporated herein by reference.

III. Heterologous Gene Expression Cassette

The invention also contemplates, for co-transformation of monocot plants, a heterologous-protein expression cassette capable of expressing a desired heterologous protein in transformed plants. The cassette is preferably one that is inducible in monocot seeds during maturation or germination.

A. Heterologous Gene. The cassette preferably includes, (i) a heterologous gene coding sequence for a selected protein of interest, (ii) upstream of the coding sequence, a monocot promoter which is induced or inducible during maturation or germination of a monocot seed, and (iii) a 3' termination sequence like that described above.

Typical proteins which are encoded by the heterologous gene include commercially important therapeutic proteins and polypeptides, including erythropoietin (EPO), tissue plasminogen activator (t-PA), urokinase and prourokinase, growth hormones, cytokines, factor VIII, epoetin-α, granulocyte colony stimulating factor, and vaccines. The coding sequence for the mature forms of these proteins are available from a variety of reference and sequence database sources.

Other heterologous proteins include polypeptides that form immunologically active epitopes, and enzymes which catalyze the conversion of intracellular metabolites, with the consequent buildup of selected metabolites in the cells. One group of proteins for use in the invention include enzymes for starch biosynthesis, including ADP glucosepyrophosphorylase (EC2.7.7.27), starch synthase (EC 2.4.1.21), and branching enzyme (R,Q). More generally, the heterologous proteins may be derived from either plant or animal sources.

B. Induced of inducible promoters. Promoters that are induced or inducible during germination include the promoters from the rice α-amylase RAmy1A, RAmy1B, RAmy2A, RAmy3A, RAmy3B, RAmy3C, RAmy3D, and RAmy3E genes, and from the pM/C, gKAmy141, gKAmy155, Amy32b, and HV18 barley α-amylase genes. These promoters are described, for example, in *ADVANCES IN PLANT BIOTECHNOLOGY*, Ryu, et al, Eds., Elsevier, Amsterdam, 1994, p.37, and references cited therein.

Representative promoters that are induced or inducible during seed-maturation conditions include those associated with the following monocot storage proteins: rice glutelins, oryzins, and prolamines, barley hordeins, wheat gliadins and glutelins, maize zeins and glutelins, oat glutelins, and sorghum kafirins, millet pennisetins, and rye secalins. One preferred promoter for expression in maturing seeds is the barley endosperm-specific B1-hordein promoter (Brandt, A., et al., (1985) Primary structure of a B1 hordein gene from barley. Carlsberg Res. Commun. 50, 333–345).

C. Other cassette elements. In addition to encoding the protein of interest, the expression cassette's gene may encode a signal/targeting/transport peptide that allows processing and translocation of the protein, as appropriate. Exemplary signal/targeting/transport sequences, particularly for targeting proteins to intracellular bodies, such as vacuoles, are signal/targeting sequences associated with the monocot maturation-specific genes: glutelins, prolamines, hordeins, gliadins, glutenins, zeins, albumin, globulin, ADP glucosepyrophosphorylase, starch synthase, branching enzyme, Em, and lea.

Another exemplary class of signal/targeting/transport sequences are sequences effective to promote secretion of heterologous protein from aleurone cells during seed germination, including the signal sequences associated with α-amylase, protease, carboxypeptidase, endoprotease, ribonuclease, DNase/RNase, (1–3)-β-glucanase, (1–3)(1–4) β-glucanase, esterase, acid phosphatase, pentosamine, endoxylanase, β-xylopyranosidase, arabinofuranosidase, α-glucosidase, (1–6) α-glucanase, perioxidase, and lysophospholipase.

As above, the heterologous gene-expression cassette may be constructed according to standard recombina/nt construction methods such as outlined in U.S. Pat. Nos. 5,889,189 and 5,888,789 noted above.

D. Set of expression cassettes. The selectable-marker expression-cassette and heterologous gene expression cassette together form a set of expression cassettes useful in cotransforming monocot plants or plant cells, in accordance with the invention, and as detailed below. This set may include two or more heterologous-gene expression cassettes, each constructed for expression of a different heterologous gene, for producing transformants that produce a panel, e.g., four or more, different heterologous proteins.

Alternatively, the selectable marker cassette and one or heterologous-gene expression cassettes may be constructed as a single expression unit containing, for example, the various expression cassettes arranged in tandem.

IV. Plant Transformation Vector Containing an Expression Cassette

The selectable-marker and heterologous-gene expression cassettes described above may be placed in a suitable expression vector designed for operation in plants. Suitable vectors are described in, for example, above-noted U.S. Pat. Nos. 5,888,789 and 5,889,189.

Expression-cassette vectors for use in the present invention include the selectable-marker expression cassette, together with companion sequences upstream and downstream from the expression cassette. The companion sequences will be of plasmid or viral origin and provide necessary characteristics to the vector to permit the vectors to move DNA from bacteria to the desired plant host. One exemplary vector is the pAPI76 vector constructed as described in Example 1A and illustrated in FIG. 1. The selectable-marker expression cassette therein includes the Gns9 promoter, an HPH coding sequence, and the RAmy1A terminator, and has the sequence identified as SEQ ID NO:2.

Figure 1B:
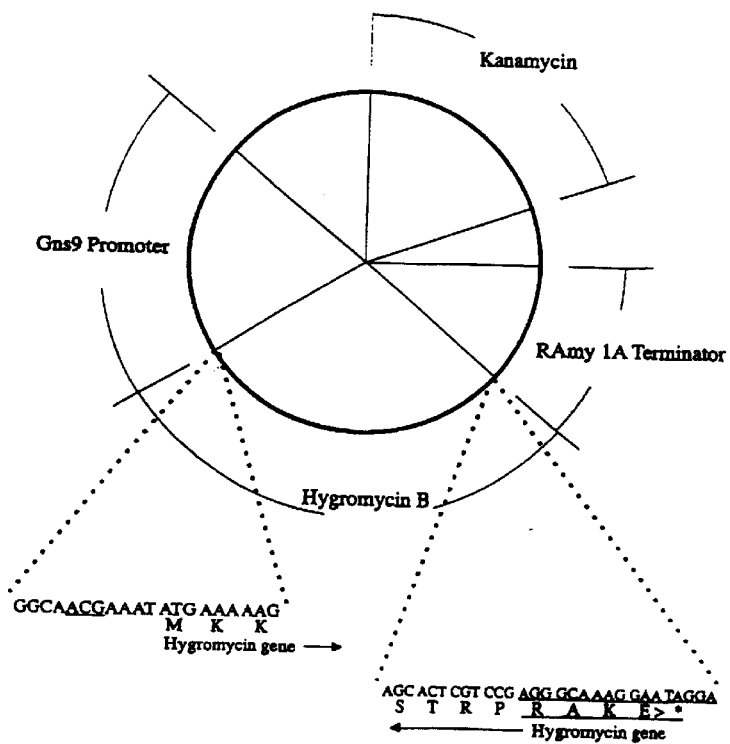
FIG. 1B shows a pAPI-146 vector like pAPI-76, constructed in accordance with another embodiment of the invention.

Another exemplary vector, designated pAPI-146, is illustrated in FIG. 1B. The construction of this selectable-marker expression cassette vector is described in Example 1B.

Both of the two vectors, and analogous vectors containing a heterologous-gene expression vector, are designed for transformation by gold-particle injection, or other direct introduction.

Figure 3A:
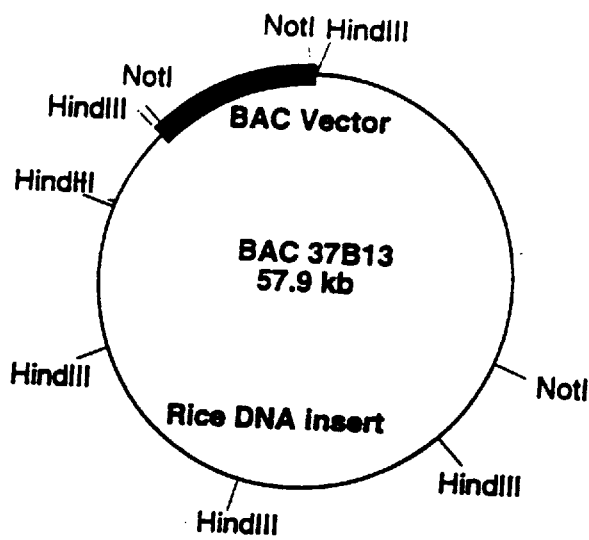
FIGS. 3A and 3B show high molecular weight (>50 kb) plasmid constructs for transformation into callus cells.

Alternatively, the transformation vector containing one or both of the selectable marker expression cassette and the heterologous gene expression cassette may be an Agrobacterium vector, such as the vector shown in FIG. 3A and described in Example 3A. This vector is exemplary of Agrobacterium vectors that can be used to transform plants via Agrobacterium infection.

In addition to the selectable marker cassette and vector, the present invention also contemplates a set of expression vectors containing the selectable-marker cassette and one or more vectors containing heterologous-gene cassettes.

V. Improved Plant Transformation Selection/Regeneration Method Utilizing the Regulated Selectable Marker Expression Cassette The plants used in the process of the present invention are derived from monocots, particularly the members of the taxonomic family known as the Gramineae. This family includes all members of the grass family of which the edible varieties are known as cereals. The cereals include a wide variety of species such as wheat (Triticum sps.), rice (Oryza sps.) barley (Hordeum sps.) oats, (Avena sps.) rye (Secale sps.), corn (Zea sps.) and millet (Pennisettum sps.), and sorghum. In the present invention, preferred family members are rice and barley.

A. Transformation

Callus cells derived from the members of the above-described plant family are co-transformed with the selectable marker vector and at least one heterologous protein expression vector containing the heterologous genes of interest, using a variety of standard techniques (e.g., electroporation, Agrobacterium, protoplast fusion, or microparticle bombardment). In the present invention, particle bombardment is the preferred transformation procedure. The heterologous protein expression vector includes a transcription regulatory region (promoter) whose transcription is upregulated in a selected tissue or plant developmental state, and/or by the presence of absence of a small molecule, such as the reduction or depletion of sugar, e.g., sucrose, in culture medium, or in plant tissues, e.g., germinating seeds.

In addition to the expression genes described above, expression cassettes constructed according to the present invention may contain sequences suitable for permitting integration of the coding sequences into the plant genome. These might include transposon sequences, and the like, for homologous recombination, as well as Ti sequences which permit random insertion of a heterologous expression cassette into a plant genome. For Agrobacterium transformations, vectors containing chimeric genes of the present invention may be modified to include T DNA sequences for Agrobacterium-mediated transfer to plant chromosomes. Further, the vectors of the invention may comprise a disarmed plant tumor inducing plasmid of Agrobacterium tumefaciens.

Methods for transforming monocot plants or plants cells are known in the literature, as represented by the following references: Li LC, Qu R D, Dekochko A, Fauquet C, Beachy R N (1993) An Improved Rice Transformation System Using the Biolistic Method. Plant Cell Reports 12:250–255; Hiei Y, Ohta S, Komari T, Kumashiro T (1994) Efficient Transformation of Rice (Oryza Sativa L) Mediated By Agrobacterium and Sequence Analysis of the Boundaries of the T-Dna. Plant Journal 6:271–282; Komari T, Hiei Y, Saito Y, Murai N, Kumashiro T (1996) Vectors carrying two separate T-DNAs for co-transformation of higher plants mediated by *Agrobacterium tumefaciens* and segregation of transformants free from selection markers. The Plant Journal 10:165–174; Armstrong C L (1999) The first decade of maize transformation: A review and future perspective. Maydica 44:101–109; Barro F, Rooke L, Bekes F, Gras P, Tatham AS, Fido R, Lazzeri P A, Shewry P R, Barcelo P (1997); Transformation of wheat with high molecular weight subunit genes results in improved functional properties. Nature Biotechnology 15:1295–1299; Battraw M, Hall T C (1991) Stable Transformation of Sorghum-Bicolor Protoplasts With Chimeric Neomycin Phosphotransferase-Ii and Beta-Glucuronidase Genes. Theoretical and Applied Genetics 82:161–168; Brettschneider R, Becker D, Lorz H (1997) Efficient transformation of scutellar tissue of immature maize embryos. Theoretical and Applied Genetics 94:737–748; Cheng M, Fry J E, Pang S Z, Zhou H P, Hironaka C M, Duncan D R, Conner T W, Wan Y C (1997) Genetic transformation of wheat mediated by Agrobacterium tumefaciens. Plant Physiology 115:971–980; Fleming G H, Kramer C M, Le T, Shillito R D (1995) Effect of Dna Fragment Size On Transformation Frequencies in Tobacco (Nicotiana Tabacum) and Maize (Zea Mays). Plant Science 110:187–192; Frame B R, Drayton P R, Bagnall S V, Lewnau C J, Bullock W P, Wilson H M, Dunwell J M, Thompson J A, Wang K (1994) Production of Fertile Transgenic Maize Plants By Silicon Carbide Whisker-Mediated Transformation. Plant Journal 6:941–948; Hagio T, Blowers A D, Earle E D (1991) Stable Transformation of Sorghum Cell Cultures After Bombardment With Dna-Coated Microprojectiles. Plant Cell Reports 10:260–264, Hamilton D A, Roy M, Rueda J, Sindhu R K, Sanford J, Mascarenhas J P (1992) Dissection of a Pollen-Specific Promoter From Maize By Transient Transformation Assays. Plant Molecular Biology 18:211–218; He D G, Mouradov A, Yang Y M, Mouradova E, Scott K J (1994) Transformation of Wheat (Triticum Aestivum L) Through Electroporation of Protoplasts. Plant Cell Reports 14:192–196 Iser M, Fettig S, Scheyhing F, Viertel K, Hess D (1999) Genotype-dependent stable genetic transformation in German spring wheat varieties selected for high regeneration potential. Journal of Plant Physiology 154:509–516; Ishida Y, Saito H, Ohta S, Hiei Y, Komari T, Kumashiro T (1996) High Efficiency Transformation of Maize (Zea Mays L) Mediated By Agrobacterium Tumefaciens. Nature Biotechnology 14:745–750; Ortiz J P A, Reggiardo M I, Ravizzini R A, Altabe S G, Cervigni G D L, Spitteler M A, Morata M M, Elias F E, Vallejos R H (1996) Hygromycin Resistance As an Efficient Selectable Marker For Wheat Stable Transformation. Plant Cell Reports 15:877–881; Pareddy D, Petolino J, Skokut T, Hopkins N, Miller M, Welter M, Smith K, Clayton D, Pescitelli S, Gould A (1997) Maize transformation via helium blasting. Maydica 42:143–154; Pukhalskii V A, Smirnov S P, Korostyleva T V, Bilinskaya E N, Eliseeva A A (1996) Genetic transformation of wheat (Triticum aestivum L.) by Agrobacterium tumefaciens. Genetika 32:1596–1600, Ritala A, Mannonen L, Aspegren K, Salmenkalliomarttila M, Kurten U, Hannus R, Lozano J M, Teeri T H, Kauppinen V (1993) Stable Transformation of Barley Tissue Culture By Particle Bombardment. Plant Cell Reports 12:435–440; Takumi S, Shimada T (1997) Variation in transformation frequencies among six common wheat cultivars through particle bombardment of scutellar tissues. Genes & Genetic Systems 72:63–69; Torbert K A, Rines H W, Somers D A (1995) Use of Paromomycin As a Selective Agent For Oat Transformation. Plant Cell Reports 14:635–640; Torbert K A, Rines H W, Somers D A (1998) Transformation of oat using mature embryo-derived tissue cultures. Crop Science 38:226–231; Walters D A, Vetsch C S, Potts D E, Lundquist R C (1992) Transformation and Inheritance of a Hygromycin Phosphotransferase Gene in Maize Plants. Plant Molecular Biology 18:189–200; Witrzens B, Brettell RIS, Murray F R, McElroy D, Li Z Y, Dennis E S (1998) Comparison of three selectable marker genes for transformation of wheat by microprojectile bombardment. Australian Journal of Plant Physiology 25:39–44; and Zhang J, Tiwari V K, Golds T J, Blackhall N W, Cocking E C, Mulligan B J, Power J B, Davey M R (1995) Parameters Influencing Transient and Stable Transformation of Barley (Hordeum Vulgare L) Protoplasts (Vol 41, Pg 125, 1995). Plant Cell Tissue and Organ Culture 43:83–83.

B. Selection/Regeneration

The improved selection/regeneration method, described in Example 2, takes advantage of the unique properties of the regulated promoter which drives expression of the selectable marker gene. The regulated promoter, as described above, strongly expresses the selectable marker gene product (e.g., HPH) in callus cells. Therefore, callus cells transformed with and expressing the selectable marker gene are able to grow in the presence of the selection agent (e.g., hygromycin B). After the transformed calli are identified and are isolated from the non-transformed calli, the transformed calli are then regenerated into plantlets in the absence of the selection agent.

To verify the conclusion that the selectable marker gene is expressed in callus, but not differentiated plant tissue, the GUS gene was placed under the control of the Gns-9 promoter and used to transform rice plant material. Expression of the GUS gene, as evidenced by a blue color, was observed in callus tissue, but no color was seen in regenerating plants or in seeds during germination. In a second test, it was verified that transformed callus tissue containing the hygromycin phosphotransferase selectable marker gene was readily selected in the presence of hygromycin B. Germinating seeds from the transformed plants, on the other hand, lacked the ability to germinate in a germination medium also containing hygromycin B, demonstrating that the seeds were expressing little if any of the selectable marker enzyme.

Specifically, it was observed that all plants in hygromycin B containing media either die or turn yellow. Two stunted plants were developed with brown roots. These plants were eventually dead due to the poor rooting system. Healthy plants were developed from calli in media without hygromycin B.

To test if transgenic seeds can gernimnate on hygromycin B containing media, 10 transgenic seeds were placed on hygromycin B containing media and 10 seeds were placed on to the same media but without hygromycin B. Seeds on hygromycin B-free media germinate and grow rapidly while the 10 transgenic seeds were not able to germinate and develop healthy plants. The reason for not being able to develop healthy plants from these transgenic calli and seeds is due to the fact that the 940 bp Gns 9 promoter was not active to express its downstream gene—hygromycin gene, in root, leaves and seeds even though these seeds and calli were from transgenic callus which were selected based on their resistance to the same concentration of hygromycin B in the media.

The novel regeneration step performed in the absence of selective pressure greatly enhances the efficiency of recovery of the transgenic plants. While not being bound by theory, the increased efficiency of recovery may be in part attributable to the absence of the selective agent, as well as the down-regulation of the selectable marker promoter in the emerging plantlets. The decreased expression of the selectable marker gene product as the calli regenerate into plantlets relieves the metabolic stress placed on the regenerating plants during this critical phase of plant transformation. In contrast, constitutive promoters remain active during this regeneration phase, placing an additional metabolic load on the plantlet and a lower efficiency of recovery.

As well as enhancing the efficiency of recovery of the emerging plantlets, the improved selection/regeneration method has additional benefits, such as substantial cost savings realized in the reduced amount of selection agent required.

VI. Simultaneous Introduction Of Multiple Heterologous Genes Into Callus Cells

The high efficiency of recovery realized by utilization of the novel selectable marker construct together with the improved selection/regeneration method described above has been found to significantly increase the probability of low-frequency transformation events, such as the introduction of multiple genes or very large DNA molecules into callus cells in a single transformation event.

Example 3 describes the successful integration of nine heterologous genes, including the selectable marker gene, introduced by simultaneous transformation with a total of nine plasmids (including the selectable marker plasmid) using the improved selection/regeneration method in conjunction with regulated promoter-selectable marker construct described above, with the results are shown in FIGS. 2A–2I. In these studies, five plants (callus cells) were transformed simulataneously with heterologous-gene expression cassettes (vectors) containing, as heterologous genes, BPN' (2A), AAT (2B), HepC (2C), HbsAg (2D), GUS (3E), GFP (2F), Hph (2G), Bar (2H), and luc (2I).

Details of the analysis of transformation is given in Example 3. Briefly, PCR analysis showed that all regenerated plants transformed, selected, and regenerated as described above carried the hph gene. Five representative transgenic plants were then subjected to Southern analysis to determine the frequency at which all nine genes co-integrated into the rice genome (FIG. 2). Integration of the genes takes place in single to multiple copies. Two of the five transgenic plants (10p-8 and 10p-34) contained DNA from all nine plasmids. The remaining plants carried DNA from seven (10p-28 and 10p-64) or eight (10p-2) of the nine co-transformed genes.

Figure 4B:
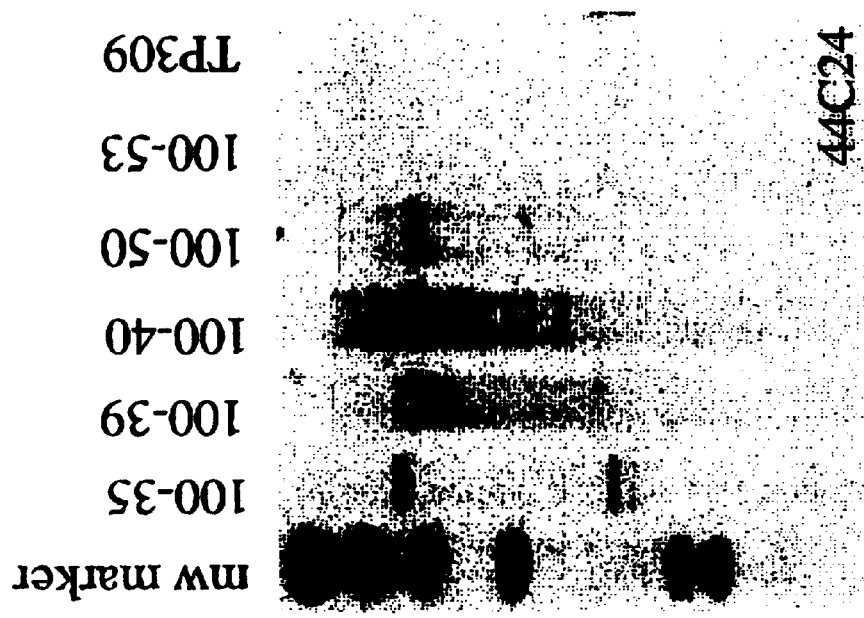
FIGS. 4A and 4B are Southern blots showing the stable integration of DNA from the high molecular weight plasmids of FIG. 3A, introduced into transgenic plants using the improved selection/regeneration method in conjunction with regulated promoter-selectable marker construct of the present invention.
Figure 4A:
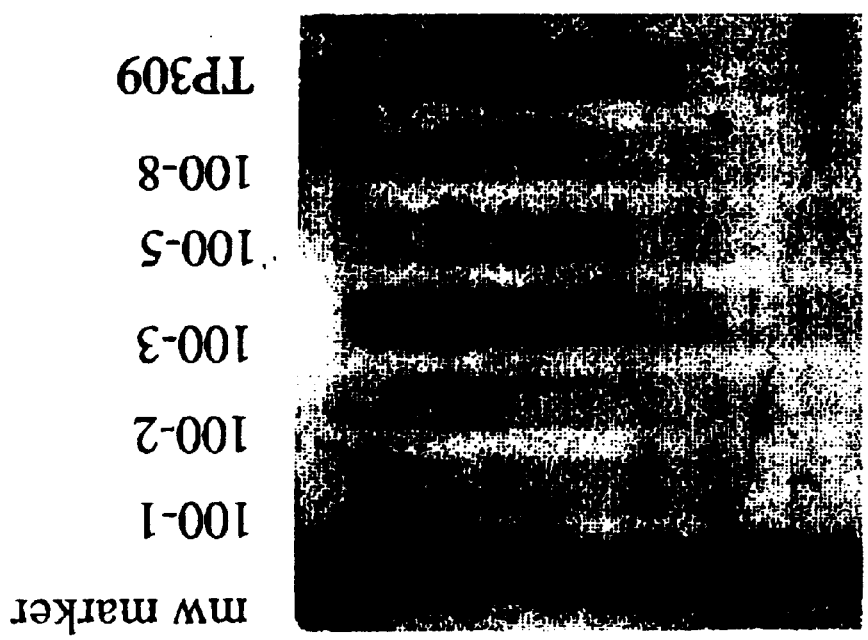

Example 4 describes the successful transformation and integration of 50 kb high molecular weight plasmids into callus cells using the improved selection/regeneration method in conjunction with regulated promoter-selectable marker construct. Exemplary results are shown in FIG. 4A and 4B.

Both the multiple plasmid transformation and high molecular weight plasmid transformation methods allow the simultaneous introduction of multiple genes into the transgenic plant. These types of transformation schemes allow, for example, metabolic engineering in monocot plants, in which the expression of numerous genes in a pathway is up-regulated and the flux of the pathway is maximized by introduction of additional homologous and/or heterologous metabolic genes.

Another application of monocot transformation with high molecular weight plasmids is for the complementation test in gene cloning by phenotype. For example, to clone the Xa2l gene, Song et al. (1995; Science 270:1804–6) identified several cosmid clones in the range of 35 to 50 kb. Limitations on the transformation technology at that time neccessitated the subcloning of these cosmids into smaller plasmids before transformation was conducted, which is rendered unnecessary by the improvement described herein.

The simultaneous transformation of monocot plant cells with multiple heterologous gene-carry plasmids, or high molecular weight plasmids, by the method of the present invention thus represents a significant technological improvement in the field of monocot plant gene expression.

The following examples are provided by way of illustration only and not by way of limitation. Those of skill will readily recognize a variety of noncritical parameters which could be changed or modified to yield essentially similar results.

General Methods

Generally, the nomenclature and laboratory procedures with respect to standard recombinant DNA technology can be found in Samb rook, et al., MOLECULAR CLONING: A LABORATORY MANUAL, Cold Spring Harbor Laboratory, Cold Spring Harbor, New York (1989) and in S. B. Gelvin and R. A. Schilperoot, PLANT MOLECULAR BIOLOGY (1988). Other general references are provided throughout this document. The procedures therein are known in the art and are provided for the convenience of the reader.

EXAMPLE 1A–1C

Selectable Marker Vector Construction

A. pAPI-76 vector

An exemplary selectable marker vector was constructed in three steps. First, a DNA fragment was amplified from the rice ce-amylase gene, RAmy1A, (Huang N. et al. (1990) Plant Molecular Biology 14: 655–668), using the primers 1AR1: 5' AAC AAT ACT GGA ATT CGA GAA GTA AAA AG 3' (SEQ ID NO:3) and 1ASma: 5° C.TA CGC AAC CCG GGA GAA AAT C 3' (SEQ ID NO:4). The amplified fragment, containing 297 bp of the RAmy1A terminator, was cloned into the SmaI/EcoRI restriction sites of pBluscript KS+, resulting in plasmid p1AT. Second, a BarmHI DNA fragment from plasmid pGL2 (Shimamoto et al. (1989)

Nature 338: 274–276) encoding hygromycin phosphotransferase (HPH) was cloned into the BamHI site of p1AT, resulting in plasmid pAPI74. The pGL2 BamH1 fragment encodes the full-length HPH polypeptide sequence minus four C-terminal amino acids. Third, a SacI/XbaI fragment was amplified from rice β-glucanase gene Gns9 using the primers gnsF, 5' GAC TTA ACT TTA GTC ATA TTT AG 3' (SEQ ID NO:5) and GnsR 5' TTC GCT CTT GCT GCT GCT CACT 3'(SEQ ID NO:6) and was inserted into the SacI/XbaI sites of pAPI74 to form pAPI76. The sequence of all fragments was confirmed by DNA sequencing.

Figure 1C:
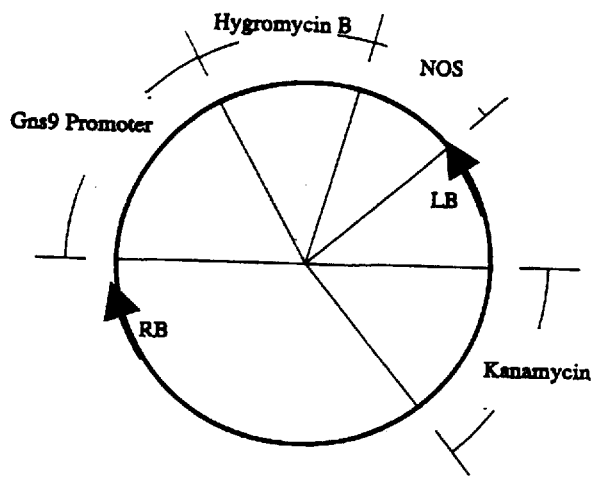
FIG. 1C shows a pAPI-353 Agrobacteriumn single-cassette vector constructed in accordance with yet another embodiment of the invention.

As shown in FIG. 1, the 5206 bp selectable marker vector described above contains a chimeric selectable marker gene comprising the Gns9 promoter, an HPH coding sequence which lacks the four C-terminal codons and stop codon of the hph gene, and an RAmy1A terminator. Since there is no stop codon in the BamHI HPH-encoding fragment, the translation reads through the HPH C-terminus into the RAmy1A terminator, generating a fusion protein with an additional C-terminal 14 amino acids (indicated in the inset of FIG. 1), most of which are hydrophilic.

B. Further improvement to pAPI-76 vector.

First, the extra ATG near the translational start codon was removed by site-directed mutagenesis (SDM), and for cloning purpose, a BamHI site was changed to BglII sites at the same time. Two site specific mutangenesis primers are synthesized:

```
API Primer#110- Hph-SDM1

BamHI(pAPI 76)
GCAGTCTAGAACTAGTAGATCTCGGGGGGCAACGAAATATGAAAAAGCC (SEQ ID NO:7)

BglII

API Primer#109    Hph-SDM2
GGCTTTTTCATATTTCGTTGCCCCCCGAGATCTACTAGTTCTAGACTGC (SEQ ID NO:8)
```

The mutagenesis was done by using PCR and Quick Change Kit from Stratgene, Calif. The resulting plasmid is called pAPI76(SDM). To repair the C-terminus of pAPI76 (SDM), the following two primers were synthesized in order to generate a PCR fragment:

```
    API Primer#111-Hph-Rev

E K A R
T AATGGATCCTCATTCCTATTC CTT TGC CCT CGG ACG AGT GCT GGG G (SEQ ID NO:9)
    BamHI stop  stop API Primer#114-Hph-fwd
      ATCGCCGCGGCTCCGGGCGTATATGC (SEQ ID NO:10)
        SacII
```

The PCR fragment that was generated with the two primers, using pAPI 76 as a template, was digested with SacII and BamHI and inserted into pAPI 76(SDM) which has been cut with SacII/BamnHI. The resulting plasmid is called pAPI106. DNA sequencing confirmed the correct site directed mutangenesis.

Both pAPI76 and pAPI106 are in plasmid backbone containing Amp resistance gene. To replace the amp gene with a kan gene, two steps were taken.

Replacement of β-Lactamase (ampicillin res.) in pUC19 with aminoglycoside phosphotransferase (kananmycin res.) from pCR2.1:

The β-lactamase gene was cut from pUC19 using SspI and DraI creating four DNA fragments of 1748, 692, 227, and 19 bp with 1748 bp fragment being the vector band to be excised. These enzymes left blunt ends at the restriction sites. The kanamycin resistance gene was amplified by the PCR from pCR2.1 with PfU polymerase thus leaving blunt ends on the PCR product for cloning into pUC19 (the 1748 fragment).

Primer-1 (KANF1) begins 146 nt upstream of the ATG for the kanr gene and primer-2 (KANR1) ends 19 nt downstream of the stop codon for the same gene.

```
                SspI half site
Primer-1 = KanF1  5'-ATTGCAAGCGAACCGGAATTGCCAG-3'  (SEQ ID NO:11)

DraI half site
Primer-2 = KanR1  5'-AAACTCTTCCTTTTTCAATTCAG-3'.  (SEQ ID NO:12)
```

Nucleotide additions were made to the PCR primers to preserve the restriction sites used for cloning. The ligation was then transformed to *E coli*, which was placed on kanamycin-containing media. Plasmids isolated from Kan resistant colonies were analyzed for the replacement of Amp gene with Kan gene. The resulting plasmid was called pUC19Kan.

To place the Gns9-hph-1A cassette into pUC19Kan, pAPI106 was double-digested with HindIII and SacI. The HindIII/SacI fragment was then isolated and inserted into pUC19Kan which was precut with HindIII and SacI. The final plasmid is called pAPI146.

C. Agrobacterium vector.

Plasmid, pJH2600, kindly provided by Dr. Diter von Wettstein, Washington State University, was used to generate a new selectable marker plasmid for cereal transformation with Agrobacterium. The vector size is about 14.3 kb. A SacI/EcoRI fragment is isolated from pAPI146 and inserted into pJH2600 cut with the same enzyme. The resulting plasmid is called pAPI352. Then the EcoR1 fragment is cut out from pAPI146 and put into pAPI352, which was digested with EcoRI as well. Plasmid with correct orientation of EcoRI fragment, is identified by DNA sequencing through the junction region of the hph gene. The plasmid is named pAPI353.

EXAMPLE 2

Rice Transformation, Selection, And Plant Regeneration

The basic procedure of microprojectile-mediated rice transformation (Sivamani E., et al. (1996) Plant Cell Rep. 15:322–327; Zhang S. et al. (1996) Plant Cell Rep. 15:465–469) was modified as follows. About 200 TP309 rice seeds were dehulled, sterilized in 50% commercial bleach for 25 min and washed with sterile water three times for 5 min each. Sterilized seeds were placed on seven plates containing N6 media (Sigma Chemical Co.; St. Louis, Mo.) to induce calli for 10 days. The primary callus was dissected and placed on fresh N6 media for three weeks. The secondary callus was separated from the primary callus and placed on N6 media to generate a tertiary callus. The tertiary callus was used for bombardment and sub-cultured 4–5 times every two weeks.

Calli 1 to 4 mm in diameter were selected and placed as a 4 cm circle on N6 media with 0.3 M mannitol and 0.3 M sorbitol for 5–24 hrs before bombardment. Biolistic bombardment was carried out with the Biolistic PDC-1000/He system (BIORAD, Richmond, Calif.). The procedure required 1.5 mg of gold particles (60 ug/ul) coated with 2.5 ug pAPI76 DNA. DNA-coated gold particles were bombarded into the rice callus with a helium pressure of 1100 psi. After bombardment, the calli were allowed to recover on the same plate for 48 hrs and then transferred to NB media with 20 mg/l hygromycin B. The bombarded calli were incubated on the selection media in the dark at 26° C. for 45 days. Transformants, which appeared opaque white, compact, and were readily distinguishable from non-transformants which were yellow-brown, soft, and watery, were selected and transferred to pre-regeneration media (PRH) consisting of N6 (without 2,4-D), 5 mg/l ABA, 2 mg/l BAP, 1 mg/l NAA and 20 mg/l hygromycin B for 9 to 12 days. The transformants were then transferred to the regeneration media (RN) consisting of N6 (without 2,4-D), 3 mg 1L BAP, 0.5 mg/L NAA and without hygromycin B, and cultured under continued lighting conditions for about two weeks. When the regenerated plants were 1 to 3 cm high, the plantlets were transferred to the rooting media which was half the strength of the MS media containing 0.05 mg/l NAA. In two weeks, the plantlets in the rooting media developed roots and its shoots grew over 10 cm. The plants were then transferred to a 2.5 in. pot containing 50% commercial soil, Sunshine #1 (Sun Gro Horticulture Inc, Wash.) and 50% natural soil. The pots were placed within a transparent plastic container to maintain 100% humidity. The plants were cultured under lighting conditions for 1 week. The transparent plastic cover was then opened little by little over one day to gradually reduce humidity, after which the plastic cover was removed completely. Water and fertilizers were added as necessary. When the plants grew to approximately 5 in. tall, they were transferred to a greenhouse to grow to maturity.

Table 1 shows the results of experiments performed to determine the correlation between integration of the selectable marker gene and integration of heterologous "target" genes carried on vectors co-transformed with the selectable marker vector. PCR analysis for stable integration of the hph selectable marker gene showed 100% of the regenerated rice plants transformed and selected as described above contained the hph gene. Various target genes (such as GUS) carried on vectors co-transformed together with the selectable marker vector also integrated with very high efficiency as confirmed by PCR analysis (Table 2) and by Southern blot analysis. Overall, 97% of the regenerated plants co-transformed with the selectable marker vector and a target vector carried the target gene in addition to the selectable marker gene.

TABLE 1

| Target vector | Selectable marker vector | Selectable marker gene | | Target gene | |
|---|---|---|---|---|---|
| | | PCR positive | PCR negative | PCR positive | PCR negative |
| pAPI65 | pAPI76 | 33 | 0 | 33 | 0 |
| pAPI72 | pAPI76 | 27 | 0 | 27 | 0 |
| pAPI96 | pAPI76 | 30 | 0 | 30 | 0 |
| pAPI85 | pAPI76 | 26 | 0 | 22 | 4 |
| pAPI98 | pAPI76 | 13 | 0 | 13 | 0 |
| pAPI90 | pAPI76 | 13 | 0 | 13 | 0 |
| pAPI64 | pAPI76 | 13 | 0 | 13 | 0 |
| pAPI78 | pAPI76 | 28 | 0 | 26 | 2 |
| totals | | 183 | 0 | 177 | 6 |

EXCAMPLE 3

Transformation of Callus Cells With Multiple Plasmids

To transform the rice calli with multiple plasmids, nine different plant transformation vectors prepared essentially as described above were selected. Eight of the plasmids contained heterologous genes, and the ninth expressed the chimeric selectable marker gene constructed as detailed above. The nine plasmids were mixed in 1:1:1:1:1:1:1:1:1 molar ratio (i.e., a ratio of heterologous vector DNA to selectable marker vector DNA of 8: 1). A total of 40 µg of the vector mixture was used to coat 48 mg gold particles and used to bombard three plates.

PCR analysis showed that all regenerated plants transformed, selected, and regenerated as described above carried the hph gene. Five representative transgenic plants were then subjected to Southern analysis to determine the frequency at which all nine genes co-integrated into the rice genome (FIG. 2). Integration of the genes takes place in single to multiple copies. Two of the five transgenic plants (10p-8 and 10p-34) contained DNA from all nine plasmids. The remaining plants carried DNA from seven (10p-28 and 10p-64) or eight (10p-2) of the nine co-transformed genes.

D. Rice Transformation With High Molecular Weight Plasmids

High molecular weight plasmids were from a bacterial artificial chromosome (BAC) library (Yang D C, et al. (1997) Theor. Appl. Genet. 95: 1147–1154). The BAC DNA and the pAPI76 selectable marker vector were mixed in a 1:1 molar ratio before coating the gold particles. Approximately 40 µg of the mixed DNA was used to coat 48 mg gold particles to bombard of three plates. Bombardment, selection, and plant regeneration were as described above.

Figure 3B:
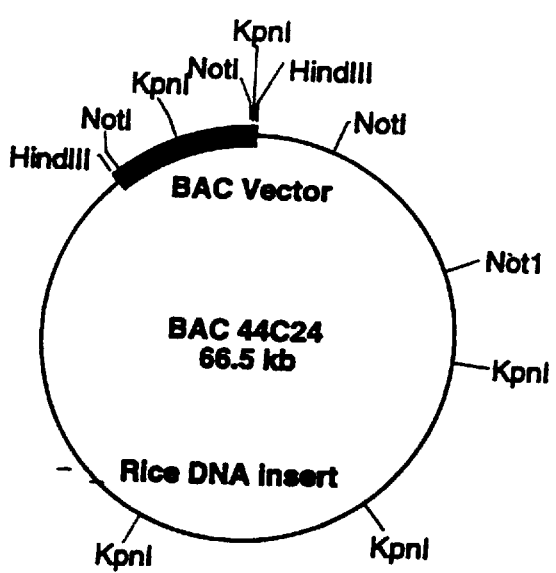
Figures 2D, 2E, 2F:
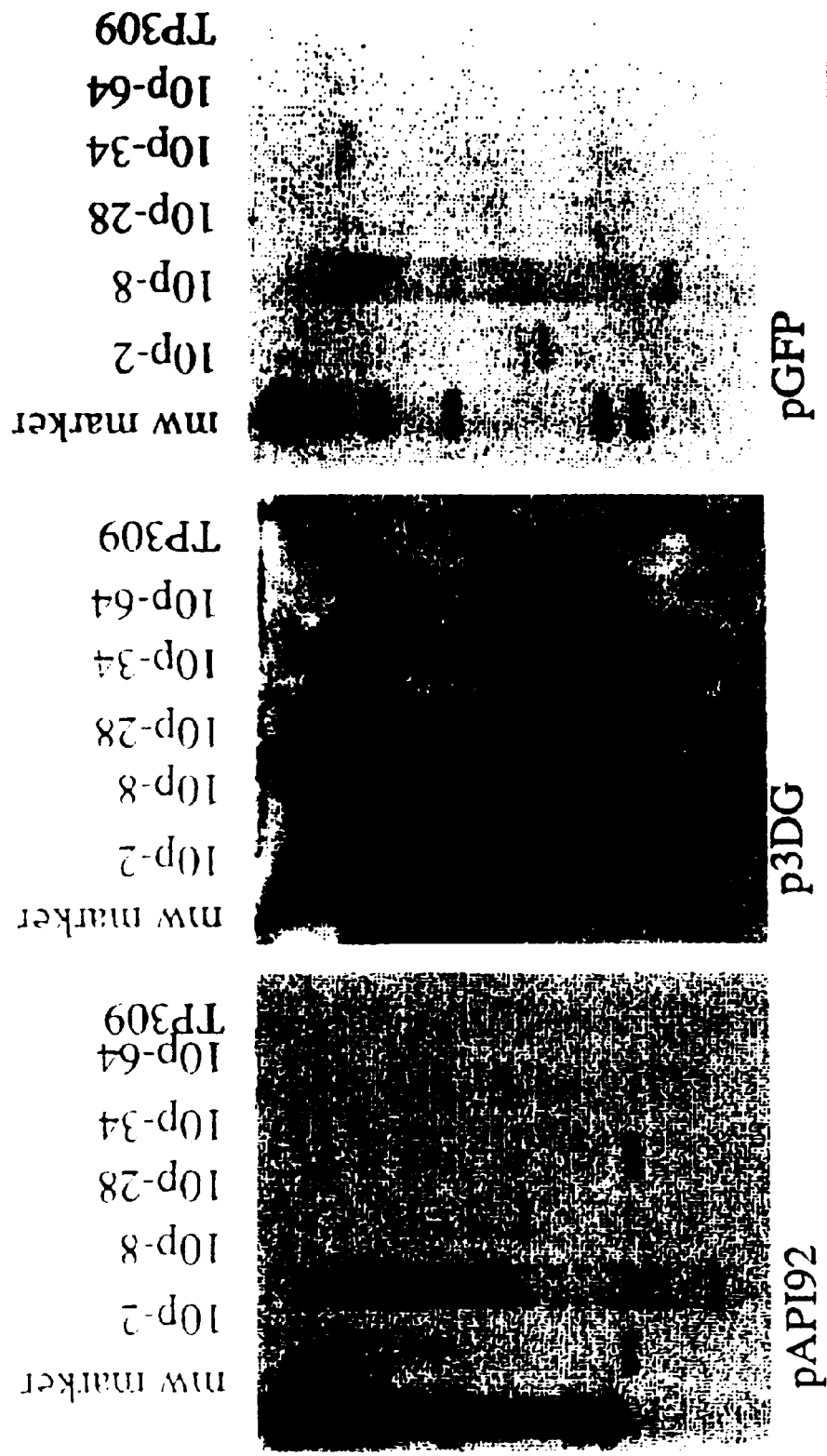

Restriction mapping indicated that the molecular weight of the two BAC clones (FIG. 3A) were over 50 kb. After transformation, seventy-seven plants were obtained. PCR analysis with hph and chloramphenicol genes showed that most of the plants carried both genes. DNA from 5 representative transgenic plants were analyzed by Southern blot (FIG. 3B). Since the inserts of BAC clones were from a rice genome (Yang et al., supra), it was difficult to distinguish transformed DNA and native DNA, therefore the vector fragment of the BAC clone was used as probe. It is assumed that if the vector DNA can integrate into rice genome, any portion of BAC DNA on the same plasmid has an equal chance to integrate into the rice genome.

It is claimed:

1. A method of transforming rice plants with one or more heterologous nucleic acid coding sequences capable of producing heterologous proteins in the rice, under selected induction conditions, comprising cotransforming rice callus cells with a set of two or more expression cassettes, said set comprising:
(a) a chimeric selectable marker expression cassette having, operatively linked in sequence in a 5' to 3' direction, (i) a transcriptional regulatory region which expresses in transformed callus cells at a significantly higher level than in seed tissue, and hybridizes under high stringency conditions with the rice β-glucanase gene (Gns9) promoter identified by SEQ ID NO:1; (ii) a hygromycin phosphotransferase encoding gene and (iii) a 3' untranslated terminator region; and
(b) at least one heterologous gene expression cassette, having operatively linked in sequence in a 5' to 3' direction, (i) a transcriptional regulatory region that is expressed, induced or inducible in plant seeds, (ii) a first DNA sequence encoding a selected heterologous protein, and (iii) a 3' untranslated terminator region, wherein the transcriptional regulatory region in said heterologous-gene expression cassette is induced during seed maturation or seed germination;

culturing the callus cells in the presence of a selection agent effective to block growth of callus cells in the absence of expression of the hygromycin phosphotransferase encoding gene;

selecting those callus cells that express hygromycin phosphotransferase, as evidenced by their growth in the presence of the selection agent; and regenerating the selected callus cells into transgenic plants under non-selection conditions.

2. The method of claim 1, wherein the transcriptional regulatory region in the chimeric selectable marker expression cassette is the Gns9 promoter identified by SEQ ID NO:1 or an operative portion thereof, said portion sufficient to promote expression in transformed callus cells at a significantly higher level than in seed tissue.

3. A rice plant transformed by the method of claim 1.

4. A plant transformation expression cassette for transforming rice plant cells with a chimeric selectable marker gene, said cassette comprising, in a 5' to 3' direction:
(i) a transcriptional regulatory region comprising a sequence which hybridizes under high stringency conditions with the rice β-glucanase gene promoter identified by SEQ ID NO:1, and which expresses in callus cells at a significantly higher level than in a selected target tissue,
(ii) a hygromycin phosphotransferase encoding selectable marker coding sequence, and
(iii) a 3' untranslated terminator region.

5. A plant transformation expression cassette according to claim 4, wherein the transcriptional regulatory region in the selectable marker gene is the Gns9 promoter identified by SEQ ID NO:1 or an operative portion thereof, said portion sufficient to promote expression in callus tissue at a significantly higher level than in a selected target tissue.

6. A plant transformation expression cassette according to claim 4, wherein said chimeric selectable marker gene has the sequence identified by SEQ ID NO:2.

7. A rice plant produced by regenerating a plant cell transformed with the expression cassette of claim 6.

8. Transgenic rice seed comprising:

a chimeric selectable marker gene including a hygromycin phosphotransferase selectable marker coding sequence under the control of a transcriptional regulatory region that is induced in callus tissue at a significantly higher level than in seed tissue and hybridizes under high stringency conditions with the rice β-glucanase gene (Gns9) promoter identified by SEQ ID NO:1, and a heterologous protein coding sequence under the control of a transcriptional regulatory region that is induced or inducible during seed maturation or germination.

9. The transgenic rice seed of claim 8, wherein the transcriptional regulatory region in the selectable marker gene is the Gns9 promoter identified by SEQ ID NO:1.

10. The transgenic rice seed of claim 8, wherein said chimeric selectable marker gene has the sequence identified by SEQ ID NO:2.

* * * * *